US010842805B2

(12) United States Patent
Gao

(10) Patent No.: US 10,842,805 B2
(45) Date of Patent: Nov. 24, 2020

(54) COMPOSITIONS CONTAINING ENRICHED NATURAL CROCIN AND/OR CROCETIN, AND THEIR THERAPEUTIC OR NUTRACEUTICAL USES

(71) Applicant: Song Gao, East Brunswick, NJ (US)

(72) Inventor: Song Gao, East Brunswick, NJ (US)

(73) Assignee: Song Gao, East Brunswick, NJ (US)

( * ) Notice: Subject to any disclaimer, the term of this patent is extended or adjusted under 35 U.S.C. 154(b) by 724 days.

(21) Appl. No.: 14/934,260

(22) Filed: Nov. 6, 2015

(65) Prior Publication Data

US 2016/0199398 A1 Jul. 14, 2016
US 2020/0016184 A9 Jan. 16, 2020

Related U.S. Application Data

(63) Continuation of application No. 14/072,998, filed on Nov. 6, 2013, now Pat. No. 9,211,298.

(60) Provisional application No. 61/727,244, filed on Nov. 16, 2012.

(51) Int. Cl.

| | |
|---|---|
| A61K 31/202 | (2006.01) |
| A61K 45/06 | (2006.01) |
| A61K 36/82 | (2006.01) |
| A61K 31/121 | (2006.01) |
| A61K 36/258 | (2006.01) |
| A61K 31/385 | (2006.01) |
| A61K 31/164 | (2006.01) |
| A61K 36/87 | (2006.01) |
| A61K 36/41 | (2006.01) |
| A61K 36/16 | (2006.01) |
| A61K 36/28 | (2006.01) |
| A61K 36/752 | (2006.01) |
| A61K 31/01 | (2006.01) |
| A61K 36/45 | (2006.01) |
| A61K 31/353 | (2006.01) |
| A23L 2/52 | (2006.01) |
| A61K 31/05 | (2006.01) |
| A61K 31/205 | (2006.01) |
| A61K 31/381 | (2006.01) |
| A61K 31/7024 | (2006.01) |
| A61K 36/744 | (2006.01) |
| A23L 33/10 | (2016.01) |
| A61K 36/484 | (2006.01) |
| A61P 1/16 | (2006.01) |

(52) U.S. Cl.
CPC ............ *A61K 31/7024* (2013.01); *A23L 2/52* (2013.01); *A23L 33/10* (2016.08); *A61K 31/01* (2013.01); *A61K 31/05* (2013.01); *A61K 31/121* (2013.01); *A61K 31/164* (2013.01); *A61K 31/202* (2013.01); *A61K 31/205* (2013.01); *A61K 31/353* (2013.01); *A61K 31/381* (2013.01); *A61K 31/385* (2013.01); *A61K 36/16* (2013.01); *A61K 36/258* (2013.01); *A61K 36/28* (2013.01); *A61K 36/41* (2013.01); *A61K 36/45* (2013.01); *A61K 36/484* (2013.01); *A61K 36/744* (2013.01); *A61K 36/752* (2013.01); *A61K 36/82* (2013.01); *A61K 36/87* (2013.01); *A61K 45/06* (2013.01); *A61P 1/16* (2018.01)

(58) Field of Classification Search
CPC ........ A61K 36/744; A61K 36/82; A23L 33/10
See application file for complete search history.

(56) References Cited

U.S. PATENT DOCUMENTS

| | | | |
|---|---|---|---|
| 7,427,622 B2 | 9/2008 | Zhao et al. | |
| 8,039,510 B2 | 10/2011 | Zhao et al. | |
| 2014/0141082 A1* | 5/2014 | Gao ...................... | A61K 31/05 |
| | | | 424/474 |

FOREIGN PATENT DOCUMENTS

| | | | | | |
|---|---|---|---|---|---|
| CN | 101811956 A | * | 8/2010 | ............. | A61K 31/05 |
| CN | 102058560 A | * | 5/2011 | | |
| EP | 1762234 A1 | * | 3/2007 | ............. | A61K 31/05 |

OTHER PUBLICATIONS

Planetary naturals: Artichoke extract. 2004. Retrieved from the Internet on: Aug. 4, 2018. Retrieved from: <URL: https://www.sourcenaturals.com/library/download/100638/>. 2 pages. (Year: 2004).*
Karmaker et al. Phytother. Res. 25: 1073-1081 (Year: 2011).*
Sun CL, et al. "Green tea, black tea and breast cancer risk: a meta-analysis of epidemiological studies." Carcinogenesis, 27(7): 1310-1315, (2006).
Leung LK, et al. "Theaflavins in Black Tea and Calechins in Green Tea Are Equally Effective Antioxidants." J. Nutr. 131: 2248-2251, (2001).
Takino Y, et al. "The structure of theaflavin, A polyphenol of black tea." Tetrahedron Letters. 45(6): 4019-4025, (1965).
Ordoudi SA, et al. "Enhanced Bioaccessibility of Crocetin Sugar Esters from Saffron in Infusions Rich in Natural Phenolic Antioxidants," Molecules, 20, 17760-17774; doi:10.3390/molecules201017760. (2015).
Albani D, et al. "Synergism Between Resveratrol and Crocin for Protection of Human Neuroblastoma SHSY-5Y Cells against Oxidative Stress." Planta Med 2013; 79-PH22 DOI: 10.1055/s-0033-1348612. (2013).
Pandey A, et al. "Synergistic Study of Antioxidant Potential of Different Spices and Their Bioactive Constituents". IJPSR, 5(8): 3267-3272. (2014).

(Continued)

*Primary Examiner* — Amy L Clark

(57) ABSTRACT

The invention relates to unique compositions containing enriched and purified natural crocin and/or crocetin for prevention and/or treatment of cancers and other conditions and diseases. Compositions comprise mainly enriched or purified natural crocin or crocetin or combination of both and possible other active phytochemicals. A composition is used as functional food, drink, dietary supplement, or therapeutic dosage to a human orally or through other appropriate way (parenteral, percutaneous, rectal, mucosal, intranasal or topical administration). A method of natural crocin and crocetin enriching and purification is revealed.

3 Claims, 3 Drawing Sheets

(56) References Cited

OTHER PUBLICATIONS

Cicero A, et al. "Short-term impact of a combined nutraceutical on cognitive function, perceived stress and depression in young elderly with cognitive impairment: a pilot, double-blind, randomized clinical trial." J. Prev. Alzheimer's Dis. 4: 12-15. (2016).

Liu JL, et al. "Systems pharmacology analysis of synergy of TCM: an example using saffron formula." Scientific Reports, 8: 380. DOI:10.1038/s41598-017-18764-2. (2018).

Mashmoul et al. "Protective effects of saffron extract and crocin supplementation on fatty liver tissue of high-fat diet-induced obese rats", BMC Complementary and Alternative Medicine. 16: 401. (2016).

Amin A, et al. "Saffron-Based Crocin Prevents Early Lesions of Liver Cancer: In vivo, In vitro and Network Analyses." Recent Patents on Anti-Cancer Drug Discovery, 11, 121-133. (2016).

Hosseini A, et al. "Effect of saffron on liver metastases in patients suffering from cancers with liver metastases: A randomized, double blind, placebo-controlled clinical trial." Avicenna J Phytomed, 5(5): 434-440. (2015).

Yousefsani BS, et al. "The mechanism of protective effect of crocin against liver mitochondrial toxicity caused by arsenic III." Toxicology Mechanisms and Methods, 28(2): 105-114. (2018).

Akbari G, et al. "The Hepatoprotective and MicroRNAs Downregulatory Effects of Crocin Following Hepatic Ischemia-Reperfusion Injury in Rats." Oxid Med Cell Longev. 2017:1702967. doi: 101155/2017/1702967. (2017).

Vali F, et al. "Synergistic Apoptotic Effect of Crocin and Paclitaxel or Crocin and Radiation on MCF-7 Cells, a Type of Breast Cancer Cell Line." International Journal of Breast Cancer, Article ID 139349, 7 pages. http://dx.doi.org/10.1155/2015/139349. (2015).

\* cited by examiner

Figure 1. Flow chart of crocin and crocetin purification

HPLC Chromatogram of crocin after crystallization from gardenia yellow.

```
Integration Result
================================================================
Signal 1 : DAD1 C, Sig=440

Peak    RT       Area      Height   Height %   Width    Area %
 #     [min]                                   [min]
----------------------------------------------------------------
  1    7.768     41.918      8.952    0.711    0.067    0.794
  2    8.075   3846.692    947.204   75.281    0.058   72.902
  3    8.299     86.275     19.069    1.516    0.064    1.635
  4    8.601    354.372     87.669    6.968    0.059    6.716
  5    8.739     34.073      9.034    0.718    0.054    0.646
  6    9.031     65.927     14.190    1.128    0.067    1.249
  7    9.148     69.984     15.920    1.265    0.063    1.326
  8    9.233     43.456      7.889    0.627    0.075    0.824
  9    9.410    209.567     32.437    2.578    0.086    3.972
 10    9.789     65.478     11.673    0.928    0.079    1.241
 11   10.021    458.774    104.192    8.281    0.063    8.695
--- -------- -------- -------- -------- -------- --------
```

Figure 3. Quantitative Nuclear Magnetic Resonance (QNMR) DMSO 400MHz
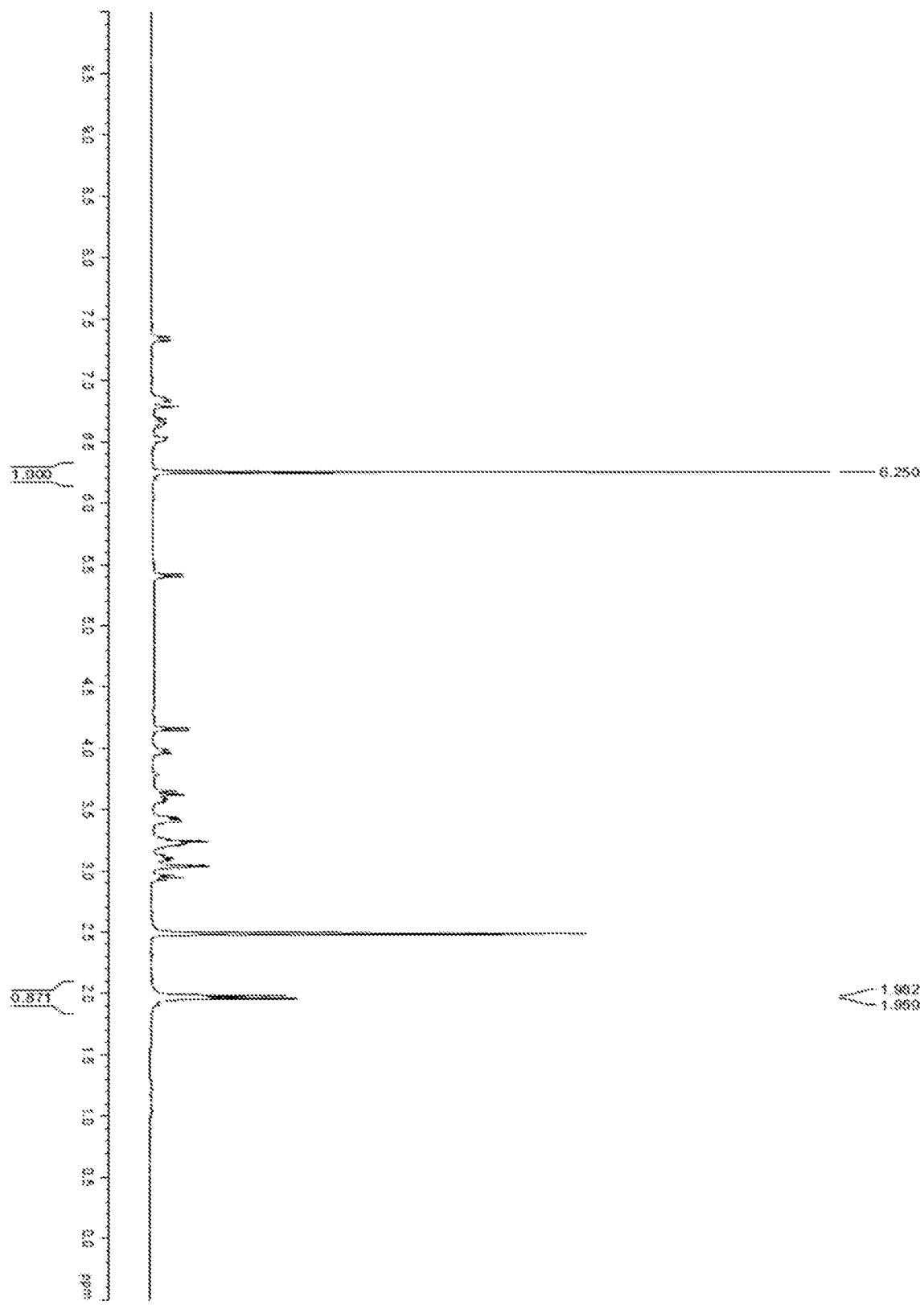

COMPOSITIONS CONTAINING ENRICHED NATURAL CROCIN AND/OR CROCETIN, AND THEIR THERAPEUTIC OR NUTRACEUTICAL USES

CROSS-REFERENCE TO EARLIER FILED APPLICATIONS

This application is a continuation of U.S. patent application Ser. No. 14/072,998, filed on Nov. 6, 2013, which claims priority to and the benefit of U.S. Provisional Application No. 61/727,244, filed on Nov. 16, 2012, the full disclosures of which are incorporated herein by reference in its entirety for all purposes.

FIELD OF THE INVENTION

The subject application relates to compositions containing enriched or purified natural crocin and/or crocetin for enhancing health and preventing or treating cancers and other diseases and health conditions.

BACKGROUND OF THE INVENTION

Cancer is the leading cause of death in the world population. In 2008, there were an estimated 12.7 million new cancer cases diagnosed and 7.6 million deaths from cancer around the world according to <<Global Cancer Facts & FIGS. 2nd Edition>>. American Cancer Society estimates in 2012 over 1.6 million new cancer cases and about 577,000 deaths resulted from cancer in the United States in "Cancer Facts & FIGS. 2012". By 2030, the global burden is expected to grow to 21.4 million new cancer cases and 13.2 million cancer deaths. Although there are a few promising options for cancer prevention, treatment mainly involves surgical removal of tumor or cancer and surrounding tissue plus chemotherapy and radiotherapy or chemotherapy alone or in combination with radiation without surgery. Various new drugs were developed for specific cancer in chemotherapy. Most often, chemotherapy is limited by severe side effects and dose limiting toxicity. Not only these chemotherapy caused side effects worsen patients' quality of life, but it can also result in stopping potentially curative treatment. So far, it still is a great challenge to find effective treatment with no/low adverse effects.

Increasing number of cancer patients uses plants, vegetables, herbs, and spices or its derived products as traditional medicine or alternative medicine. At least half of cancer patients in the United States use complementary and alternative medicine, exclusively or concurrently with traditional therapeutic regime such as radiation therapy and/or chemotherapy. It is ideal to develop drug or treatment from in fruits, vegetables, herbs and spices that are efficacious and without adverse side effect. Most preferably, a product or products can be invented to prevent development of various cancers and other diseases. This invention relates to improvements in human nutrition and therapeutics involving providing unique compositions with enriched or purified natural crocin and crocetin and/or other phytochemicals constituting anti-cancer compositions which can prevent, reduce and treat cancer as well as prevent or treat other diseases and conditions, including age-related and neurodegenerative disorders such as Alzheimer's and Parkinson's diseases, cardiovascular and cerebrovascular disease, digestive system diseases, toxin and alcohol caused liver injuries. The compositions can be used alone against cancer and protect normal cells and organs, or used in combination with other chemotherapy in a synergistic fashion that serve as sensitizer to more effectively kill abnormal cells while protect normal cells and organs at lower chemo dose, or in combination with radiotherapy against cancers and protect normal cells and organs undergoing radiation.

Crocin and crocetin exist in *Crocus*. They are the chemical components with antioxidative properties primarily responsible for the color of the stigmas of *Crocus sativus* L. (Saffron). Crocetin is a carotenoid dicarboxylic acid with 20 carbon atoms and it is the core of crocin. Crocin, in general term, includes Crocin-I (Crocetin-di-beta-D-gentiobiosyl ester), Crocin-II (Crocetin-beta-D-gentiobiosyl-beta-D-glucosyl ester), Crocin-III (Crocetin-mono-beta-D-gentiobiosyl ester), Crocin-IV (beta-D-monoglucoside ester of monomethyl alpha-crocetin), Crocetin-di-(beta-D-glucosyl) ester, Crocetin-mono-beta-D-glucosyl ester. Crocin mainly exists in trans-form, but can also present in cis-form in minor amount.

To demonstrate a few, chemical structure of crocetin (alpha-crocetin) is shown below:

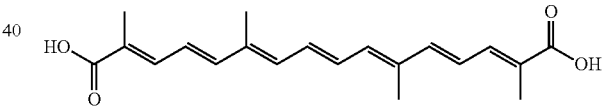

Chemical structure of Crocin-I (Crocetin-di-beta-D-gentiobiosyl ester) is shown below:

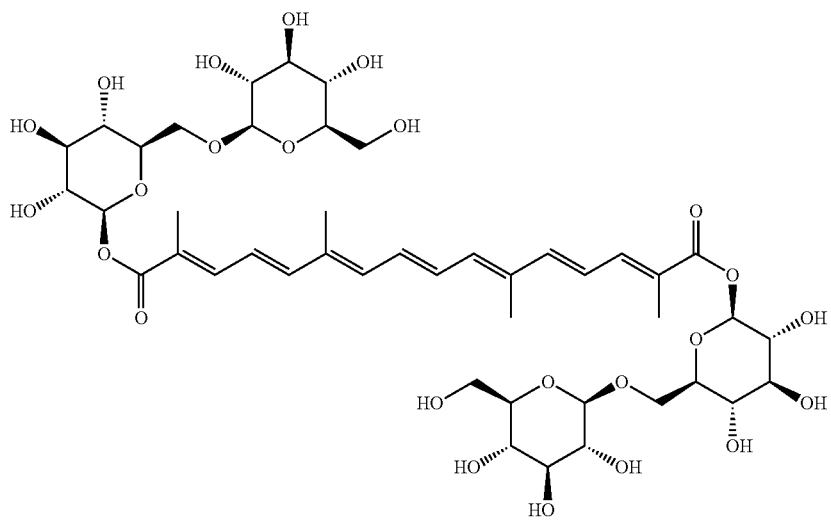 [SMILES: CC(/C=C/C=C(\C)C(=O)O[C@@H]1O[C@H](CO[C@@H]2O[C@H](CO)[C@@H](O)[C@H](O)[C@H]2O)[C@@H](O)[C@H](O)[C@H]1O)=C\C=C\C=C(C)\C=C\C=C(/C)C(=O)O[C@@H]1O[C@H](CO[C@@H]2O[C@H](CO)[C@@H](O)[C@H](O)[C@H]2O)[C@@H](O)[C@H](O)[C@H]1O]

Chemical structure of Crocin-II (Crocetin-beta-D-gentiobiosyl-beta-D-glucosyl ester) is provided below:

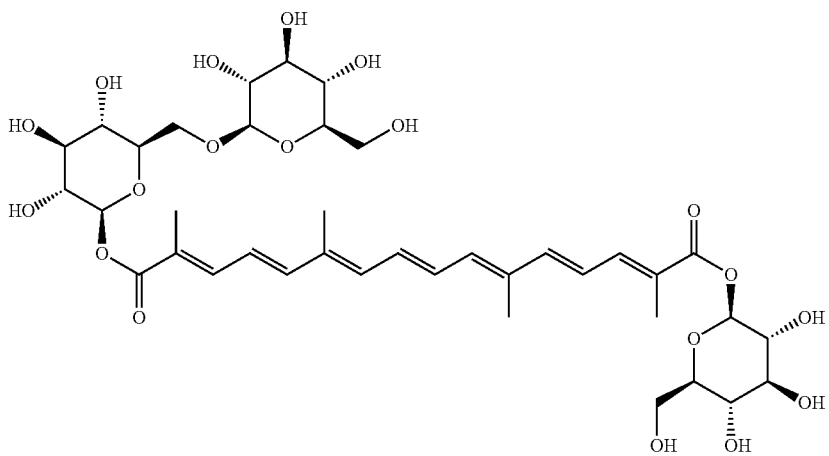 [SMILES: CC(/C=C/C=C(\C)C(=O)O[C@@H]1O[C@H](CO)[C@@H](O)[C@H](O)[C@H]1O)=C\C=C\C=C(C)\C=C\C=C(/C)C(=O)O[C@@H]1O[C@H](CO[C@@H]2O[C@H](CO)[C@@H](O)[C@H](O)[C@H]2O)[C@@H](O)[C@H](O)[C@H]1O]

Chemical structure of Crocin-III (Crocetin-mono-beta-D-gentiobiosyl ester) is shown below:

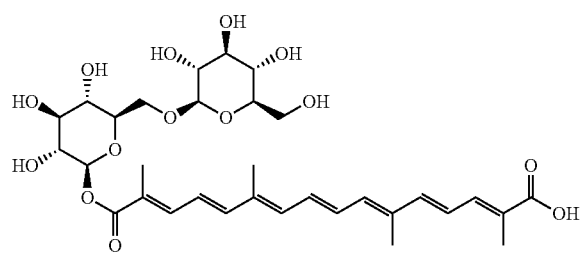 [SMILES: CC(/C=C/C=C(\C)C(=O)O)=C\C=C\C=C(C)\C=C\C=C(/C)C(=O)O[C@@H]1O[C@H](CO[C@@H]2O[C@H](CO)[C@@H](O)[C@H](O)[C@H]2O)[C@@H](O)[C@H](O)[C@H]1O]

Saffron is used as coloring and flavoring agents in the preparation of food in different parts of the world and has been used since ancient times for strengthening digestion, relieving coughs, smoothing menstruation, relaxing muscle spasms, improving mood, calming anxiety, preventing depression and enhancing men's sexual ability. Saffron is also used as health tonic. It is believed that regular intake of saffron with milk helps to build resistance against common cold and asthma. In recent years, Saffron is reported to possess anti-oxidant and anti-cancer effects among a wide range of pharmacological activities (Abdullaev F I. 2002, Chermahini S H. 2010, and Bhargavak V. 2011).

Commercial saffron is produced in Azerbaijan, France, Greece, India, Iran, Italy, Spain, China, Israel, Morocco, Turkey, Egypt, and Mexico from dried stigmas of cultivated *Crocus sativus* L. Each flower has only three small stigmas. It takes about 75,000 flowers to produce one pound of saffron. Currently, Saffron is produced worldwide at an annual rate of about 300 tons and harvested by hand, making Saffron an extremely expensive commodity with very limited supply. Saffron is safe to use. Saffron and saffron extracts have been safely used as spice, food coloring or for medicinal purposes for hundreds of years. Saffron is regarded as a food by Joint FAO/WHO Expert Committee on Food Additives (TRS 733-JECFA 29/33) and listed as substance Generally Recognized As Safe (GRAS) by FDA [CITE: 21CFR182.10, Revised as of Apr. 1, 2012].

Another source of crocin and crocetin is the *gardenia* fruit, *Gardenia jasminoides* Ellis or *Gardenia augusta* Merrill var. *grandiflora* Hort. Content of crocin in *gardenia* fruits increases when ripening. *Gardenia* fruits have been used in China and Japan as traditional medicine for its antiphlogistic, diuretic, and cholagogic effects. *Gardenia* fruit is listed and approved in 1998 by Chinese government both as food and as medicine and listed in The Japanese Pharmacopoeia as crude drug and in the list of existing food additives (Yoshiaki Kato 2000). Its extract, *gardenia* yellow, has also been listed as INS. 164 by JECFA (1989) as a food additive for colorant and widely used to give yellow color to food products such as noodle, pasta, candy, beverage and pickled products in Japan. *Gardenia* yellow has almost the same crocin and crocetin derivatives as saffron, only different in composition ratio of crocin and crocetin derivatives (Carmona M. 2006, Chen Y. & Zhang H. 2008).

Studies have shown saffron extracts have anti-cancer activities. The anticancer/antitumor properties of crude extracts of saffron have been demonstrated in vitro and in vivo (Nair S C 1991, 1994, Abdullaev F I. 2002, 2003, Chryssanthi D G. 2007, Bakshi H. 2010). Crocin in saffron causes apoptosis in different type cancer cells. It is of great interest that non-tumor cells in culture appear to be insensitive to the effects of such extracts compared with tumor cells. Even saffron extract was found to stimulate or support in vivo growth of normal human lung cells (Abdullaev F I, 1992a,b).

Saffron aqueous extract rich in crocin was found protect animal against genetic damage induced by anti-cancer agents (Premkumar K. 2006). In this study, to ascertain the chemoprotective potential of saffron against the genotoxicity of three well-known anti-tumor drugs—cisplatin (CIS), cyclophosphamide (CPH) and mitomycin C (MMC)—using comet assay, Three doses of saffron (20, 40 and 80 mg/kg b.w.) were orally administered to mice for five consecutive days prior to the administration of anti-tumor drugs under investigation. Pre-treatment with saffron significantly inhibited anti-tumor drugs induced cellular DNA damage (strand breaks) as revealed by decreased comet tail length, tail moment and percent DNA in the tail.

Formation of toxic amyloid structures is believed to be associated with various late-onset neurodegenerative disorders such as Alzheimer's and Parkinson's diseases. One human study (Akhondzadeh 2010) was carried out to investigate saffron may inhibit the aggregation and deposition of amyloid β in the human brain and may therefore be useful in Alzheimer's disease (AD). Fifty four patients were screened for a 22-week, double-blind study of parallel groups of patients with mild to moderate AD. The psychometric measures, which included AD assessment scale-cognitive subscale (ADAS-cog), and clinical dementia rating scale-sums of boxes, were performed to monitor the global cognitive and clinical profiles of the patients. Patients were randomly assigned to receive capsule saffron 30 mg/day (15 mg twice per day) (Group A) or donepezil 10 mg/day (5 mg twice per day) for a 22-week study. Saffron at this dose was found to be effective similar to donepezil in the treatment of mild-to-moderate AD after 22 weeks, while the donepezil group experienced significant frequency of vomiting.

Alcohols or ethanol over consumption is known to impair learning and memory. The acute effects of an alcohol extract of *Crocus sativus* L (saffron) were studied on learning and memory in step through and step down tests in normal as well as in learning- and memory-impaired mice (Zhang 1994). Saffron extract reduced the ethanol-induced impairment of memory registration both in step through and step down tests and the ethanol-induced impairment of memory retrieval in step down test. Saffron extract decreased the motor activity and prolonged the sleeping time induced by hexobarbital. It was suggested that saffron extract ameliorates the impairment effects of ethanol on learning and memory processes, and possesses a sedative effect. In behavioral and electrophysiological studies (Abe K. 2000), Saffron extract improved ethanol-induced impairments of learning behaviors in mice, and prevented ethanol-induced inhibition of hippocampal long-term potentiation, a form of activity-dependent synaptic plasticity that may underly learning and memory. This beneficial effect of saffron extract is attributed to crocin (crocetin di-gentiobiose ester), but not crocetin. It was indicated that Saffron extract or its active constituents, crocetin and crocin, could be useful as a treatment for neurodegenerative disorders accompanying memory impairment.

Dietary saffron was found in animal study (Maccarone R. 2008) maintains morphology and function after exposure to damaging light in mammalian retina. The photoreceptor layer was largely preserved in saffron-treated animals. Rate of photoreceptor death induced by the damaging bright continuous light drastically reduced in saffron treated animals. Saffron supplement was found to improve retinal flicker sensitivity in early age-related macular degeneration (AMD) (Falsini B. 2010). Followed up clinical study in Italy and Australia supported saffron supplementation and indicated crocin and crocetin as key actives to provide sustained benefits to central retinal function for AMD patients (Piccardi M. 2012)

Though saffron is reported to possess anti-oxidant and anti-cancer effects among a wide range of pharmacological activities, it is these main components, crocin and crocetin that were indicated to provide these pharmacological activities. Due to the very limited source and expensiveness of saffron, it is unrealistic to produce large scale of highly enriched crocin and crocetin from saffron. Saffron quality and its content of crocin and crocetin vary significantly, range from less than 1% to 20% (Alonso G L. 2001, Lechtenberg M. 2008). Quantification study of saffron also indicated a high amount of adulterant on the saffron market (Lechtenberg M. 2008). Chemically synthesized crocetin and its salts are not natural and not identical to natural crocin and crocetin, and may possess very different biologically and pharmacologically properties. *Gardenia* fruits, *gardenia* extracts, or *gardenia* yellow provide a feasible source to enrich and purify industrial scale of natural and high purity crocin and/or crocetin for wide applications. Enrich and purified crocin and/or crocetin render means to quantitatively and consistently deliver the actives in formulated products for preventing and treating cancers and other diseases.

Many other phytochemicals (organic chemicals from plant source) also have extensive and variety of health benefits in preventing or treating diseases or cancers. A few examples are provided here. Resveratrol in grape has been studied and reported to have anti-cancer effects, anti-inflammatory effects, cardiovascular benefits, anti-diabetes potential, energy endurance enhancement, and protection against Alzheimer's (Baur J A 2006). Curcuminoids, include curcumin, demethoxycurcumin, and bisdemethoxycurcumin, are polyphenolic pigments found in the spice turmeric. Curcumin has been widely studied and indicated to have anticancer, anti-inflammatory, antiviral, hypocholestrolemic and break-up of beta-amyloid plaques in brain activities (Aggarwal B B. 2007). Tea polyphenols, including catechin, epicatechin, epicatechin gallate, epigallocatechin, epigallocatechin gallate, theaflavin, theaflavin-3,3'-digallate, theaflavin-3-gallate, etc. and extracts have also been studied and showed extensive health benefits including anticancer, cholesterol-lowing, anti-inflammatory, anti-aging, and against atherosclerosis and coronary heart disease, high blood cholesterol concentrations, and high blood pressure (Mukhtar H. 2000). Anthocyanins are a category of phytochemicals in fruits and vegetables that give them vivid red to blue. Based upon many cell-line studies, animal models, and human clinical trials, Anthocyanins have been suggested possess anti-inflammatory and anti-carcinogenic activity, cardiovascular disease prevention, obesity control, diabetes alleviation, and eye health promoting properties (He J 2010, Kalt W 2010). Human studies with diet rich in anthocyanins suggest it may also protect against development of Parkinson's disease and improve blood pressure (Cassidy J. 2011, Gao X. 2012).

Prior arts have been mostly focused on purify shingle crocin component, either crocin-1 (alpha-crocin) or crocetin. CN102516325 A revealed a method of producing crocin with higher than 95% purity from *gardenia*. The prior art specifically produces one single crocin component, crocin I (called crocin in prior art) to purity at least 95%. WO2004078695 A1 revealed a method for purification of crocetin. Method in this prior art includes steps of hydrolysis of crocin and then purification of crocetin. Prior arts also include methods of extracting, changing profile of crocin and crocetin or improving recovery of saffron colorant recovery. WO2010094745 A1 and US2010/0210572A1 revealed a method of producing hydrolysate of crocin, resulting in crocin related products with significant amount of crocetin mono esters. WO2004056201 A1 revealed a method of increased colorant (crocin and crocetin) recovery from saffron raw material to 95%, while crocin and crocetin together having a pigment concentration of 15-24%. Crocetin and its salts have been chemically synthesized (WO2006104610 A2, U.S. Pat. No. 7,351,844 B2). But these chemically synthesized crocetin and its salts are not natural and may not have the same biological and pharmacological properties. US20130156746 A1 revealed a dietary supplement composition which comprises saffron powder and resveratrol. Because saffron has many different grades and varies in its crocin content, it is very difficult to use such a composition for products require quality and efficacy consistency. US20110236481 A1 revealed a composition contains safranal and/or crocin and/or picrocrocin from saffron plant or saffron as satiety agent for treatment of obesity. The active contents of safranal and/or crocin and/or picrocrocin are used at low or diluted level by weight compare to saffron in products and showed to be effective in suppressing hungry (Gout B. 2010).

Applications of enriched and purified natural crocin and/or crocetin enable quality consistency and quantitative amount of crocin and/or crocetin in products. Its use alone or use in combination with other health beneficial phytochemicals in nutraceutical or therapeutic composition is useful in preventing and treating many cancers and disease as well as enhancing health. Combinations of crocin and/or crocetin with other phytochemicals also offer synergistic and broader benefits in preventing and treating cancers and diseases. The invention is focused on crocin and/or crocetin that are extracted, enriched or purified from natural source, *gardenia* fruits, *gardenia* extracts or *gardenia* yellow, to formation unique nutraceutical or pharmaceutical compositions with or without other health promoting phytochemicals, and their uses for (a) prevention or treatment of diseases and conditions including cancers, neurodegenerative diseases, heart diseases, liver diseases, kidney diseases, eye diseases, metabolic syndrome, atherosclerosis, arthritis, inflammations, obesity, or diabetes, etc.; (b) protection of liver, heart, kidney, and other normal organs from injuries or damages; (c) improvement or enhancement of learning/memory ability, immune system, skin health, anti-aging, and over all health.

SUMMARY OF THE INVENTION

Saffron provides many health benefits and has been safely used for thousand years, but quality of saffron and the content of key actives, crocin and crocetin, vary significantly. Enriched and purified natural crocin and/or crocetin of this invention reduce or eliminate undesirable components in saffron or *gardenia* fruits. It provides means to deliver quantitatively and consistently effective amount of crocin and/crocetin in compositions or formulated products for preventing and/or treating cancers and other diseases as well as enhancing and improving health. High purity crocin and/or crocetin is particular advantageous in a composition for injectable products.

It is an object of the invention to provide compositions and a means for improving/enhancing cancer prevention, treatment and reducing cancer risk as well as improving other conditions and diseases.

It is an object of the invention to provide compositions and a means for improving/enhancing/restore cells, tissues, and organ functions of cancer suffer patients. Improve and prolong life span.

It is an object of the invention to provide compositions and a means for improving/enhancing therapeutical effectiveness of other cancer drugs through synergistic effects or as sensitizer or enhancer, reducing drug resistance.

It is an objective of the invention to provide compositions and a means for improving/protecting non-cancerous or normal cells, tissues, organs and patients from injury, damage by other anti-cancer agents, toxins, chemotherapeutic agents, radiation.

It is an object of the invention to provide compositions and a means for improving/enhancing healthy aging and mental health, particularly responses in central nerve system that slow, prevent, and mitigate neurodegenerative disorders such as Alzheimer's and Parkinson's diseases; inhibit producing neurotoxins, inhibit acetylcholine breakdown, prevent formation of toxic amyloid structures; enhance brain function, have an effect of improved quality of life.

It is an object of the invention to provide compositions and a means for improving/enhancing learning and memory and cognitive abilities; reduce oxidative stress damage to the hippocampus induced by chronic stress.

It is an object of the invention to provide compositions and a means for improving/treating ethanol/alcohol-induced impairments of learning and memory and cognitive abilities; improve/treat neurodegenerative disorders accompanying memory impairment.

It is an object of the invention to provide compositions and a means for protecting/improving/enhancing heart function/structure/composition, particularly responses that improve cardiac arrhythmia and antioxidant systems, prevent the myocardial infarction and relieve myocardial stunning; improve/enhance recovery of heart function.

It is an object of the invention to provide compositions and a means for improving/enhancing human health, particularly responses that reduce chronic inflammation and prevent inflammatory conditions; provide treatments that will be simple and effective and will have little or no adverse side effects.

It is an object of the invention to provide compositions and a means for improving/enhancing human health, particularly responses that improve and enhance immune system and, thereby, having an effect of regulating/boosting the health of human.

It is an object of the invention to provide compositions and a means for improving/enhancing human health, particularly responses that treat and reduce serum triglyceride, total cholesterol, low density lipoprotein (LDL) cholesterol and very low density lipoprotein (VLDL) cholesterol level.

It is an object of the invention to provide compositions and a means for improving/enhancing liver function/activities, particularly responses that protect, prevent liver injury from alcohols, toxins, metal or heavy metal over dose; protect liver from chemo agent injury and damage. Maintain and enhance recovery of liver function.

It is an object of the invention to provide compositions and a means for improving/enhancing liver health, particularly responses that improve/enhance liver recovery from injury and shock, thereby, having an effect of maintaining/boosting health of human.

It is an object of the invention to provide compositions and a means for improving/enhancing kidney function/activities, particularly responses that protect, prevent kidney injury and damage; maintain and enhance recovery of kidney function.

It is an object of the invention to provide compositions and a means for improving/enhancing eye health, particularly responses that slow/prevent/treat age related macular degeneration; increase blood flow to the retina and choroid, also facilitate retinal function recovery thereby preventing ischemic retinopathy and age related macular degeneration.

It is an object of the invention to provide compositions and a means for improving/enhancing human health, particularly responses that improve diabetic benefits, inhibit insulin resistance or insensitivity induced by fat or various fatty acids or high sugar diets; restore/maintain normal pancreatic functions/orders, prevent glucose toxicity.

It is an object of the invention to provide compositions and a means for improving/enhancing human health, particularly responses that prevent/treat obese and associated diseases/conditions.

It is an object of the invention to provide compositions and a means for improving/enhancing human health, particularly responses that reduce/prevent/treat atherosclerosis, thereby, having an effect of regulating/boosting the cardiovascular health and lowering cholesterol; prevent/treat coronary artery disease and peripheral vascular disease.

It is an object of the invention to provide compositions and a means for improving/enhancing human health, particularly responses that improve sense of well-being and, thereby, having an effect of calming, prevent/improve depression.

It is an object of the invention to provide compositions and a means for improving/enhancing skin health and appearance, particularly responses that improve skin conditions in anti-aging, anti-wrinkle, anti-inflammation, anti-oxidation, restore/prevent/treat skin damage and the signs of aging of the skin.

It is an object of the invention to provide specific combinations of ingredients or formula containing enriched or purified natural crocin and/or crocetin that deliver bioactive components which directly, effectively prevent/treat/benefit cancer/tumor patients.

It is another object of one aspect of the invention to provide improvements of human nutrition by the combinations, in particular specially formulated to enhance bioactives intakes.

It is another object of one aspect of the invention to provide improvements of human nutrition by the combinations, in particular specially formulated with enriched or purified natural crocin and/or crocetin to effectively prevent/protect risk of cancers, treat/benefit cancer/tumor patients.

It is another object of one aspect of the invention to provide improvements of human nutrition by the combinations, in particular specially formulated with enriched or purified natural crocin and/or crocetin to improve/protect non-cancerous or normal cells, tissues, organs and patients from injury/damage by other anti-cancer agents, toxins, chemotherapeutic agents, radiation.

It is another object of one aspect of the invention to provide improvements of human nutrition by the combinations, in particular specially formulated with enriched or purified natural crocin and/or crocetin to effectively prevent/treat/benefit neurodegeneration patients; prevent/slow/treat Alzheimer's and Parkinson's diseases.

It is another object of one aspect of the invention to provide improvements of human nutrition by the combinations, in particular specially formulated with enriched or purified natural crocin and/or crocetin to effectively prevent/treat/benefit patients with impairment in learning and memory; improve/enhance learning and memory.

It is another object of one aspect of the invention to provide improvements of human nutrition by the combinations, in particular specially formulated with enriched or purified natural crocin and/or crocetin to effectively enhance/improve heart health, treat individuals with heart illness or sub-normal conditions.

It is another object of one aspect of the invention to provide improvements of human nutrition by the combinations, in particular specially formulated with enriched or purified natural crocin and/or crocetin to effectively inhibit inflammations, chronic inflammations which may lead time many health problems.

It is another object of one aspect of the invention to provide improvements of human nutrition by the combinations, in particular specially formulated with enriched or purified natural crocin and/or crocetin to enhance/improve immune system.

It is another object of one aspect of the invention to provide improvements of human nutrition by the combinations, in particular specially formulated with enriched or purified natural crocin and/or crocetin to enhance/improve human circulation system, lower cholesterol, triglyceride and low density lipoprotein.

It is another object of one aspect of the invention to provide improvements of human nutrition by the combinations, in particular specially formulated with enriched or purified natural crocin and/or crocetin to enhance/improve liver health, protect/prevent liver injury/damage from alcohol/ethanol, toxins, chemotherapeutic agent. Strengthen/restore liver functions.

It is another object of one aspect of the invention to provide improvements of human nutrition by the combinations, in particular specially formulated with enriched or purified natural crocin and/or crocetin to effectively enhance/improve eye health, prevent/slow/treat individuals with age-related illness or sub-normal conditions.

It is another object of one aspect of the invention to provide improvements of human nutrition by the combinations, in particular specially formulated with enriched or purified natural crocin and/or crocetin to enhance and benefit individuals with diabetes.

It is another object of one aspect of the invention to provide improvements of human nutrition by the combinations, in particular specially formulated with enriched or purified natural crocin and/or crocetin to enhance and benefit individuals with coronary artery disease and peripheral vascular disease; to prevent and reduce risk of coronary artery disease and peripheral vascular disease.

These and other objects are achieved by the invention, which provides food/dietary/therapeutic compositions/formula comprising unique combinations of enriched or purified natural crocin and/or crocetin and regimens employing them to enhance and maintain health and improve sub-health conditions.

These and other objects are achieved by the invention, which provides therapeutic compositions/formula comprising unique combinations of enriched or purified natural crocin or crocetin alone or both in combination with other excipient or stabilizer to prevent or treat cancers/tumors.

These and other objects are achieved by the invention, which provides food/dietary/therapeutic compositions comprising unique combinations of natural enriched crocin and crocetin and possible other bio-actives, proteins, peptides and amino acids constituting immune system improving nutraceutical compositions and regimens employing them to reduce risks in individuals with suppressed/abnormal immune systems.

These and other objects are achieved by the invention, which provides food/dietary/therapeutic compositions comprising unique combinations of natural enriched crocin and crocetin and possible other bio-actives, vitamins constituting antioxidant nutraceutical compositions and regimens employing them to reduce risks of diseases These and other objects are achieved by the invention, which provides food/dietary/therapeutic/topical compositions comprising unique combinations of natural enriched crocin and crocetin and possible other bio-actives, constituting antioxidant nutraceutical compositions and regimens employing them to reduce risks of radical damages, chemical damages and photo-damages to normal cells, tissues, organs, (liver, skin, etc.).

It is also an objective of this invention to provide a method to enrich or purify crocin and/or crocetin from *gardenia* fruit, *gardenia* extract, *gardenia* yellow, or saffron.

BRIEF DESCRIPTION OF THE FIGURES

FIG. 3 shows a QNMR chromatogram of crocin obtained as described in Example 2.

DETAILED DESCRIPTION OF INVENTION

Figure 1:
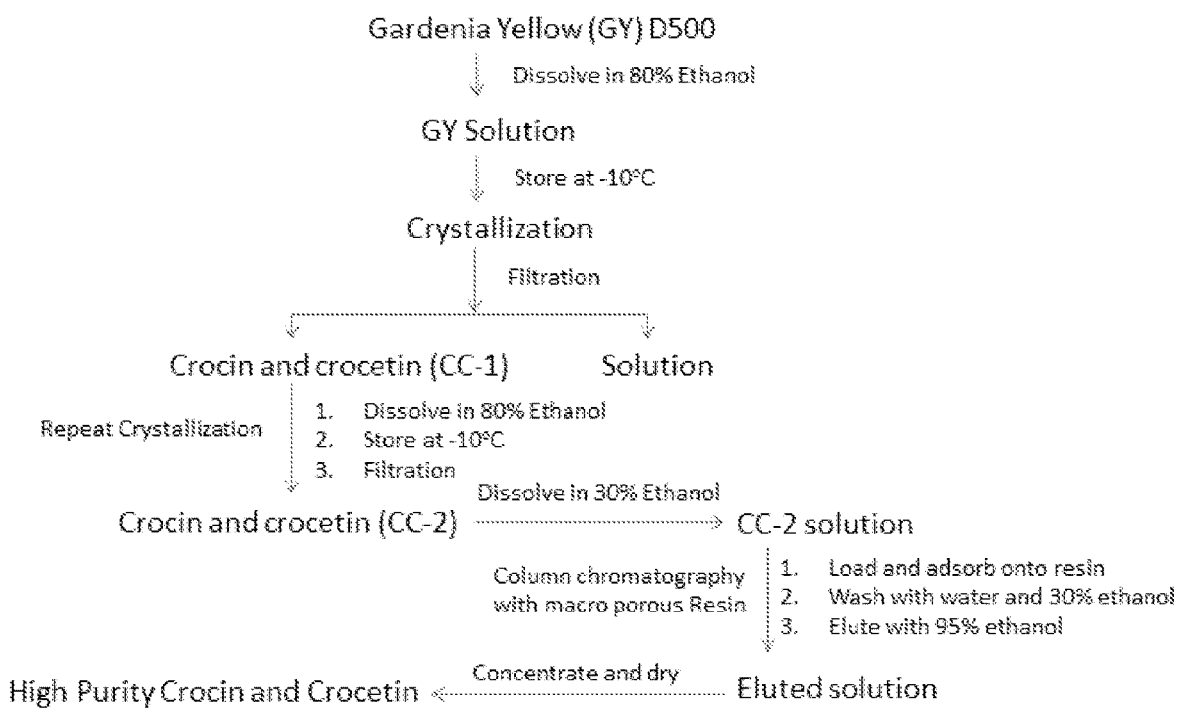
FIG. 1 shows the flow diagram of crocin enriching and purification from *gardenia* yellow D500 as described in Example 1.

While various embodiments of the present invention about compositions are discussed below, it should be appreciated that the present invention provides some of many applicable inventive concepts that can be embodied in a wide variety of specific contexts. The specific embodiments discussed herein are merely illustrative of a few specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

This invention reveals nutraceutical/therapeutic compositions/formulations and/or regimens comprising unique combinations with meaningful, quantitative, and sufficient amount of enriched or purified or high purity natural crocin and/or crocetin and possible other health beneficial phytochemicals and/or extracts and/or vitamins and/or health beneficial minerals.

This invention to provide a safe and natural nutraceutical/therapeutic composition for preventing, decreasing and treating cancers, age-related neurodegenerating disease (Alzheimer's and Parkinson's diseases), brain, heart, liver, kidney diseases, eye and circulations diseases, diabetes, inflammations, skin damages, signs of aging of the skin and other conditions. This invention provides a safe and natural nutraceutical/therapeutic composition for enhancing/restoring function of brain, heart, liver, eye, kidney, pancreas, skin and protecting them from oxygen radical stress, toxins, metals, alcohol/ethanol induced injury/damage/impairment. This invention provides a safe and natural nutraceutical/therapeutic composition for enhancing/restoring in learning and memory. This invention prevents/improves/treats above mentioned diseases and conditions by the use of a specific composition or compositions of crocin and/or crocetin or combination of crocin and crocetin and possible selection of other effective or health promoting phytochemicals, amino acids, vitamins or minerals. The invention is also useful but not limited to above mentioned diseases, disorders and sub-health conditions. These compositions can be considered as a therapy. These compositions can also be considered as improvements in human nutrition in that they present new combinations of phytochemicals, or amino acids, or vitamins useful in reducing above mentioned disease risks.

Crocin and other crocetin glycosides are major color components and phytochemicals of the stigmas of saffron (*Crocus sativus* L.) and the fruits of *gardenia* (*Gardenia jasminoides* Ellis). Both saffron and *gardenia* fruits have been traditionally used and listed as food additives. Crocin, crocetin and crocetin natural glycosides from saffron or *gardenia* fruits are considered safe as extensive studies found crocin have no toxic effect on normal cells and protect normal cells. Due to limitation of saffron source and its expensiveness, it is cost forbidden to commercially enrich or purify crocin and/or crocetin from saffron. Saffron quality variation and a high amount of adulterant on the saffron market also hinder its use in quality products. Enriching and purification of crocin and crocetin from commercial *gardenia* yellow, *gardenia* extract or directly from *gardenia* fruits provides affordable and high purity crocin and/or crocetin for quantitative and amount consistent applications in this invention. The enriched and purified crocin and/or crocetin of this invention to be used in supplements or therapeutic products are safe and effective for enhance health, protect, prevent and lower risk of above mentioned diseases and conditions. Use of enriched or purified natural crocin and/or crocetin in therapeutic compositions or formulations is essential in this invention. Particularly an injectable requires high purity and high quality crocin and/or crocetin.

The crocin and/or crocetin used in this invention is the enriched or purified form with crocin and/or crocetin content of at least 50%, preferably at least 80%, more preferably at least 90%, in particular cases at least 99%, manufactured under conditions to meet food or pharmaceutical standards. Said the crocin can include Crocin-I (Crocetin-di-β-D-gentiobiosyl ester), Crocin-II (Crocetin-β-D-gentiobiosyl-β-D-glucosyl ester), Crocin-III (Crocetin-mono-β-D-gentiobiosyl ester), Crocin-IV (β-D-monoglucoside ester of monomethyl α-crocetin), Crocetin-di-(β-D-glucosyl) ester, Crocetin-mono-β-D-glucosyl ester, β-cis-crocetin di(β-D-gentiobiosyl) ester and β-cis-crocetin β-D-gentiobiosyl-β-d-glucosyl ester, etc. naturally existed crocetin derivatives in saffron or *Gardenia* fruits.

This invention has a number of advantages over the use of saffron and saffron extracts. Because crocin and/or crocetin can be enriched and purified from an abundant and safe source, *gardenia* yellow, *gardenia* fruit or *gardenia* extract through a simple and effective method, the manufactured crocin and/or crocetin are highly enriched and purified in comparison to saffron. Processes described herein, without using toxic solvent or generating large amount of waste, are environmentally friendly. Enriched and purified crocin and/or crocetin with purity at least 50% up to 99% have significant reduced or no undesirable components provide safer products. Unlike saffron which varies in crocin content, Crocin and/or crocetin described in compositions herein provide quantitative, quality consistent and effective dosage for preventing and treating cancers, neurodegenerative disorders such as Alzheimer's and Parkinson's diseases, age-related macular degeneration, and other diseases or conditions. High purity crocin and/or crocetin described herein are particularly useful in compositions for injection or infusion.

Crocin and/or crocetin are typically analyzed and detected by HPLC at wavelength of 440 nm. However, if a component or components in a saffron or *gardenia* extract possess no crocetin or carotenoid-like core structure, such components will not be detected at 440 nm. Hence, to determine crocin purity in saffron or *gardenia* extracts, it is essential to analyze the sample or samples with crocin standard at different concentrations to establish a linear line under the same conditions on a HPLC instrument. Preferably, crocin purity determination can also be done by Quantitative Nuclear magnetic resonance (NMR) spectroscopy.

An exemplary embodiment method of the invention includes but is not limited, for example:

a. Purification of Crocin and/or Crocetin:

20 g of Commercial *gardenia* yellow D500 was weighed into a centrifuge bottle, add 3 times of 80% ethanol in volume of *gardenia* yellow weight, cover the bottle and stir at 35° C. for 15 to 20 minutes in dark, separate soluble in supernatant after centrifugation at 10,000×g for 10 minutes, supernatant was collected in flask, repeat 5 times of the addition of ethanol dissolution and separation of soluble supernatant, the collected and combined supernatants was sealed and put into −10° C. freezer in dark for 15 to 20 days, then filter to separate crystals from solution and washed with acetone, 5.7 g crocin was obtained, dissolve this crocin in 360 ml 80% ethanol and recrystallize at −10° C. give purer crocin, wash with acetone, dry to obtain about 4 g; high purity crocin is further obtained by column chromatography through common steps including dissolving the product in 30% ethanol, passing the solution through a column filled with macroporous resin A-5 to adsorb crocin with resin, washing with distilled water and 30% ethanol to remove impurities, eluting the column with 95% ethanol to desorb pure crocin from the resin, collecting the eluted crocin solution, concentrating and drying. A flow chart of crocin and/or crocetin purification is shown in FIG. 1.

Analysis of Crocin by HPLC:

Preparation of linear solution: Accurately weighed 11.9 mg Crocin I standard in 10 ml volumetric flask, add methanol and water (1:1) to dissolve crocin and make to the scale as mother solution. Aliquot the prepared mother solution to make a series of diluted standard solutions. Standard solutions were subjected to HPLC analysis to prepare standard curve. 5 μml of the prepared solution was injected into HPLC instrument. HPLC instrument is an Agilent 1260/6120 and equipped with Agela Venusil XBP C18 column (4.6×150 mm, 5 μm) and column temperature at 40° C. Other conditions and elution gradient were listed below:

Mobile Phase: A: 4 L H2O (with 1.5 ml TFA)
B: 4 L Acetonitrile (with 0.75 ml TFA)
Gradient:

| Time (min) | B % |
|---|---|
| 0.01 | 0 |
| 10.00 | 60 |
| 15.00 | 100 |
| 20.00 | 100 |

Post run: 4.5 min
Flow rate: 1 ml/min
Wave length: 440 nm
Column Temp: 40° C.

Corresponding HPLC peak areas and concentrations of crocin samples were listed in table 1:

TABLE 1

| Crocin Standards | Peak area | Conc (μg/ml) |
|---|---|---|
| Std. 1 | 3119.7 | 119 |
| Std. 2 | 2004.7 | 79.33 |
| Std. 3 | 1507.4 | 59.5 |
| Std. 4 | 735.6 | 29.75 |
| Std. 5 | 168.8 | 7.44 |

A linear equation of y=26.361x−48.186 ($R^2$=0.9994) was obtained by calculation. Sample with crocin concentration in the range of 7.44 μg/ml and 119 μg/ml conforms to the linear relation.

b. Analysis of Crystallization Sample:

Accurately weigh 18.8 mg crystallization sample in 10 ml volumetric flask, add methanol and water (1:1) to dissolve sample and make to the scale resulting in 188 m/ml (18.8 mg/10 ml) concentration, and accurately transfer 5 ml into another 10 ml volumetric flask, add methanol and water (1:1) to scale and make 94 μg/ml sample concentration; 50 of the prepared sample solution was injected to HPLC under same conditions described in making standard linear equation (see FIG. 1); Calculate sample purity by using the formula of:

Crocin Purity (100%)=Concentration of the solution under test/Concentration of crocin samples*100

Measured and calculated results by HPLC method are shown in table 2.

TABLE 2

Figure 2:
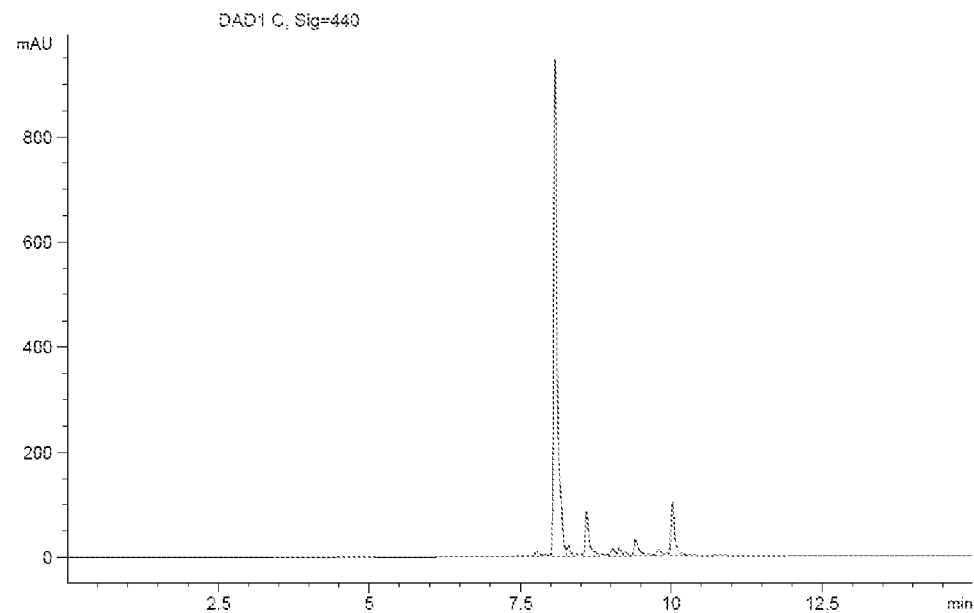
FIG. 2 shows HPLC chromatograms of crocin obtained as described in Example 2.

| Sample | Area | C1 (μg/ml) | W (mg) | C2 (μg/ml) | Purity % |
|---|---|---|---|---|---|
| 1 | 3846.7 | 147.75 | 18.8 | 188 | 78.59 |
| 2 | 1886 | 73.37 | 9.4 | 94 | 78.06 | c. Analysis of Crocin by QNMR:

Accurately weigh 5-10 mg of crystallization sample and maleic acid into NMR tube, add 0.6-1.0 ml of DMSO-d6 (>99% atom-% D) into the tube and shake to dissolve both sample and maleic acid. It is subjected to quantitative H-NMR analysis. NMR instrument is Varian 400MR. Test for measurement is set at Pulprog=zg45, d1=15, d2=19, and nt=16. δ 1.97 (12H) is selected as quantification peak; δ 6.25 is internal standard quantification peak (see FIG. 2). After measurement, results are calculated by the formula:

Assay of sample=[$I(a) \times MW(a) \times N(b) \times W(b) \times A(b)$]/[$I(b) \times MW(b) \times N(a) \times W(b)$]

I(a): Area of sample selected peak
I(b): Area of internal standard peak
MW(a): Sample molecular weight
MW(b): Internal standard molecular weight
W(a): Sample weight
W(b): Internal standard weight
N(a): Number of proton of selected sample peak
N(b): Number of proton of selected internal standard peak
A(b): Purity of internal standard Measured and calculated results by QNMR method are shown in table 3.

TABLE 3

| Test No. | Sample Wt. (mg) | Standard Wt. (mg) | Ratio of area of selected peak to standard's | Purity of Sample |
|---|---|---|---|---|
| 1 | 9.7 | 6.2 | 0.795:1 | 77.30% |
| 2 | 9.4 | 6.9 | 0.871:1 | 81.10% |
| Average | | | | 79.20% |

The nutraceutical/pharmaceutical compositions with enriched or purified crocin and/or crocetin of the invention can be formed alone or in combination with one or more of health promoting phytochemicals or food extracts containing effective amount of phytochemicals including: acteoside, aloenin, aloesin, aloin, alpinetin, atractylenolide, atractylodin, aurantio-obtusin, cimigenol, cimifugin, cimiside, garcinone, ascorbic acid, astragalin, quercetin, resveratrol, pterostilbene, curcumin, demethoxycurcumin, bisdemethoxycurcumin, theaflavin, theaflavin-3,3'-digallate, theaflavin-3-gallate, theaflavin-3'-gallate, L-theanine, anthocyanidins, anthocyanins, catechin, epicatechin, gallocatechin, epigallocatechin, epicatechin gallate, gallocatechin gallate, epigallocatechin gallate, procyanidin, chlorogenic acid, cardamonin, arctigenin, arctiin, asiatic acid, asiaticoside, bergamotin, bergapten, betaine, dioscin, galangin, cimicifugoside, cinnamic acid, ferrulic acid, fumaric acid, α-lipoic acid, carnosine, L-carnitine, caffeic acid, ellagic acid, maslinic acid, phenylethyl caffeate, caffeic acid phenethyl ester, theobromine, theophylline, caffeoylquinic acid, ursolic acid, allicin, gingerol, shogaol, ginkgolide, ginkgetin, ginsenoside, astragaloside, cycloastragenol, danshensu, danshenol, danshenxinkun, tanshinone, tanshindiol, rosmarinic acid, dosmin, nobiletin, tangeretin, luteolin, lutein, β-lycopene, zeaxanthin, tyrosol, hyperin, hyperoside, quercetin, quercetrin, isoquercitrin, hydroxytyrosol, rosarin, β-rosasterol, rosavin, rosin, punicalagin, punicalin, myricetin, myricitrin, kaempferol, dihydromyricetin, apigenin, naringin, naringenin, honokiol, magnolol, mangiferin, mangostin, hesperetin, hesperidin, lupeol, indole-3-carbinol, genistein, genistin, daidzin, daidzein, cynarin, bilobalide, bilobetin, epimedin, sulforaphane, phloretin, phloretin-xyloglucoside, phloridzin, proanthocyanidins, procyanidin B1, procyanidin B2, procyanidin C1, silibinin, rutin, wogonin, morin, morusin, mulberroside A, mulberroside B, glycyrrhizic acid, glycyrrhetinic acid, linarin, protodioscin, protogracillin, synephrine, rebaudioside A, stevioside, vitexin, isovitexin, vitexin-4, vitexin-4"-O-glucoside, vitexin-2"-O-rhamnoside, vitexin-4'-rhamnoside, alpha-tocopherol, beta-tocopherol, gamma-tocopherol, delta-tocopherol, etc.

A food extract that should contain effective amount of phytochemicals can come from one but not limited to the following sources: bilberry, blueberry, cranberry, raspberry, cherry, mulberry, pomegranate, purple corn, strawberry, grapes, black berry, gooseberry, black currants, grape, cocoa beans, coffee beans, pine bark, cardamom, cinnamon bark, *ginseng*, astrgalus, rodiola, garcinia, ginger, ginkgo, citrus fruit, grape skins, grape seeds, hawthorn, artichoke, broccoli, broccoli seeds, apple, olive, orange, lemon, pepper, soybean, mango, tea leaves, tomato, turmeric, cabbage, purple corn, black rice, bitter lemon, *stevia*, lo han, goji (wolfberry), sea buckthorn, kudzu, clove, hemp, *cassia, magnolia*, nutmeg, jujube, honeysuckle, poria, bellflower, lotus, basil, sesame, *angelica*, cimicifuga, epimedium, schisandra, *salvia*, licorice, *ligustrum*, ophiopogonis, aloe, dodder, fenugreek, gotu kola, purslane, tribulus, etc. The above components of the compositions of the invention should have, individually, effective levels of purity to meet the objectives of the invention. The components can be standardized for dosage level based on purity and amount used.

The nutraceutical/pharmaceutical compositions can further include one or more free amino acids or peptides, such as arginine, lysine, methionine, histedin, leucine, isoluceine, alanine, phenyalanine, asparingine, aspartic acid, tryptophane, proline, threonine, cysteine, selenocysteine, serine, taurine, tyrosine, valine, glycine, glutamine, glutamic acid, ornithine, carnosine, L-carnitine, glutathione.

The nutraceutical/pharmaceutical compositions can further include one or more vitamins or minerals, including, but not limited to, vitamin A, vitamin C, vitamin B1, vitamin B2, vitamin 33, vitamin B6, vitamin B12, vitamin D, vitamin E, vitamin K (and derivatives), calcium, sodium, potassium, chromium, vanadium, magnesium, manganese, selenium, copper, molybdenum, boron, vanadium, and/or iron (and derivatives)(preferably in amounts less than the RDA).

The nutraceutical/pharmaceutical composition of the invention may be administered in any route that is appropriate, including but not limited to oral, parenteral (Intravenous, intramuscular, intraperitoneal, intrasternal, subcutaneous, intraarticular injection and infusion), percutaneous, rectal, mucosal, intranasal or topical (transdermal, as by powders, ointments, creams, sprays, drops or patches) administration. Ophthalmic formulation, ear drops, solutions, and eye ointments are also contemplated as being within the scope of this invention. The most suitable route may depend upon the condition and disorder of the recipient.

In certain embodiments more than one dose comprising an effective amount of crocin and crocetin is administered to the human (e.g., two or more doses spaced over time, each dose comprising an effective amount of crocin and crocetin). The effective amount of crocin and crocetin can be in compositions in combination with one or more active components of phytochemicals and or amino acids or peptides previously mentioned.

In some embodiments compositions comprise with one or more carbohydrate nutrients. For example, the carbohydrate nutrient may be selected from the group consisting of: rice oligodextrin, amylase, amylopectin, glucose, sucrose, fructose; maltodextrin, maltose, isomaltulose, leucrose, trehalulose, ribose, trehalose.

The applications and dosage forms of nutraceutical/pharmaceutical compositions for oral administration can be liquids, beverages, tablets, soft gels, capsules, pills, caplets, gums, dragees, granules, powders, or effervescent tablets, sprays, functional foods.

A solid nutraceutical/pharmaceutical composition for oral administration may optionally contain, in addition to the above enumerated nutraceutical/pharmaceutical composition ingredients or compounds: carrier materials such as corn starch, acacia, gelatin, malt, tragacanth, microcrystalline cellulose, kaolin, dicalcium phosphate, calcium carbonate, sodium chloride, alginic acid, lactose, glucose, sucrose, and the like; disintegrators including, microcrystalline cellulose, alginic acid, and the like; binders including acacia, methylcellulose, ethyl cellulose, sodium carboxymethylcellulose, polyvinylpyrrolidone, hydroxypropyl methylcellulose, and the like; and lubricants such as magnesium stearates, stearic acid, silicone fluid, talc, oils, waxes, colloidal silica, and the like. In addition to active ingredients, an effervescent tablet composition may contain mixtures of acids (like citric, tartaric, malic and fumaric acid or combination thereof) and carbonates like sodium, potassium bicarbonate or carbonate that release carbon dioxide when dissolved in water and water soluble binder (starches, natural gums, cellulose gums, microcrystalline cellulose, methylcellulose, cellulose ethers, ethylcellulose, sodium carboxymethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof) and lubricant (sodium benzoate, polyethylene glycol, L-leucine, adipic acid, and combinations thereof). A composition can also include other ingredients including, e.g., flavor agents, fillers, surfactants, color agents, and sweeteners. The usefulness of such excipients is well known in the art. A composition optionally comprises one or more additional coatings surrounding the core and/or the control releasing coat such as moisture barrier coats, enteric coats or coatings that affect the physical integrity and/or appearance of the nutraceutical composition.

In the case of capsules, tablets and pills, the dosage form may also comprise buffering agents. Solid compositions of a similar type may also be employed as fillers in soft and hard-filled gelatin capsules using lactose or milk sugar as well as high molecular weight polyethylene glycols and the like.

A liquid nutraceutical composition for oral administration in connection with a method can be prepared in water or other aqueous vehicles. In addition to the above enumerated nutraceutical/pharmaceutical composition ingredients or compounds, a liquid nutraceutical/pharmaceutical composition can include suspending agents such as, for example, alginates, pectin, kelgin, carrageenan, acacia, methylcellulose, polyvinyl alcohol, polyvinylpyrrolidone, and the like. The liquid nutraceutical/pharmaceutical compositions can be in the form of a solution, emulsion, syrup, gel, powder or elixir including or containing wetting agents, sweeteners, and coloring and flavoring agents. Various liquid and powder nutraceutical compositions can be prepared by conventional methods.

The nutraceutical/pharmaceutical compositions for parenteral and percutaneous administration comprise pharmaceutically acceptable sterile aqueous or nonaqueous solutions, dispersions, suspensions or emulsions and sterile powders for reconstitution into sterile injectable solutions or dispersions. Intravenous administration is likely one of the best routes in delivery of crocin and crocetin for most effective prevention and treatment of cancers and other diseases and conditions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Further, the injections may contain stabilizers, solubilizers, suspending agents, emulsifiers, soothing agents, buffers, preservatives, isotonic agents, antibacterial and antifungal agents, etc. The injectable compositions are sterilized in the final formulation step or prepared by sterile procedure. The nutraceutical/pharmaceutical composition of the invention may also be formulated into a sterile solid preparation, for example, by freeze-drying, and the sterile solid preparation can be dissolved in a solvent, sterile injectable water, injectable saline or other sterile diluent(s), to form an injectable solution for immediate injection.

A pharmaceutical composition solution for parenteral administration may generally be prepared by dissolving the compound in a medium, subjecting the resulting solution to filtration for sterilization, filling the solution in vials or ampoules or glass bottles or suitable plastic bags, and sealing the vials or ampoules or bottles or bags. It is also possible to freeze-dry the composition and fill the resulted powder in vials, and then eliminate the moisture in vacuum to improve stability. Parenteral suspensions can be prepared by substantially the same method as that applied to solutions for parenteral administration; however, the suspensions can preferably be manufactured by suspending the active ingredient in a medium, and then subjecting the result to sterilization by using ethylene oxide or the like. Furthermore, surface active agents, moistening agents and so forth may also be added so that a uniform dispersion of the active ingredient can be obtained.

Compositions for rectal administration are preferably suppositories which can be prepared by mixing the active components of this invention with suitable non-irritating carriers such as cocoa butter, polyethylene glycol or a suppository wax which are solid at ambient temperature but liquid at body temperature and therefore melt in the rectum and release the active compound.

Compositions for topical or transdermal administration of this invention can be prepared as ointments, pastes, creams, lotions, gels, powders, solutions, sprays, inhalants or patches. The active component is admixed under sterile conditions with a pharmaceutically acceptable carrier and any needed preservatives or buffers as may be required. The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compositions of this invention may also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes may be used. The present compositions in liposome form may contain, in addition to the active components of this invention, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

In certain embodiments the amount of crocin or crocetin or the combination of both is from about 1.0 mg to about 7000 mg per dose, from about 50 mg to about 500 mg per dose for prevention and protection, or from about 200 mg to about 2000 mg per dose, or from about 200 mg to 500 mg per dose. In certain embodiments the effective amount of crocin and crocetin is from about 0.25 mg/kg bodyweight of the human to about 50 mg/kg bodyweight of the human per dose. The dose, and perhaps the dose frequency, can vary according to the age, body weight and conditions of individual patient. The purity of the ingredients and the presence of added diluents, emulsifiers and other additives must be taken into consideration in determining the dosage.

In a preferred form the invention provides a dietary supplement composition wherein supplement capsules are prepared by simply use of dry or solid compositions as filler in soft and hard-filled gelatin or vegetable capsules for oral administration. Prepared capsules are orally administered as part of a prepared food. One example formula includes the following active ingredient presented in parts in weight: about 200 parts crocin and crocetin, about 150 parts green tea extract, about 50 parts curcumin, about 50 parts resveratrol, about 25 parts *Panax ginseng* extract, about 15 parts α-lipoic acid, and about 10 parts L-carnitine. A composition containing this formula and carriers may be conventionally presented in unit dosage form and prepared by methods, fill in as capsules or press into tablets, well known in the art of supplement. The total daily dose (in single or divided doses) ranges from about 100 mg per day to about 2000 mg per day, or about 200 mg per day to about 4000 mg per day. In some embodiments, the total daily dose may range from about 50 mg to about 5000 mg per day. A powder mixture of this formula can also be used to prepare functional foods. More examples provided later.

In another preferred form the invention provides a therapeutic composition wherein soluble effervescent tablets are prepared by compression. Compare to conventional tablet and capsules, effervescent tablets have major advantage that the drug product is already in solution at the time it is consumed. The absorption is faster and active ingredients are delivered to the stomach at a pH that is just right for absorption. Because effervescent tablets dissolve fully in a buffered solution, it prevents gastric acids from interacting with the active ingredients and reduces causes of stomach and esophageal upsets. Effervescent tablets also enhance the absorption of a number of active ingredients, compared to conventional formulations. This is because the carbon dioxide created by the effervescent reaction can induce enhanced active-ingredient permeability due to an alteration of the paracellular pathway. The paracellular pathway is the primary route of absorption for hydrophilic active ingredients in which the solutes diffuse into the intercellular space between epithelial cells. It is postulated that the carbon dioxide widens the intercellular space between cells, which leads to greater absorption of active ingredients. One examped formula includes: 1500 mg citric acid, 800 mg potassium bicarbonate, 800 mg sodium bicarbonate, 160 mg sodium carbonate, 250 mg crocin and crocetin, 60 mg polyethylene glycol 6000, 50 mg aspartame, 30 mg flavorant. The material of this formula can be blended and pressed into appropriate size of soluble effervescent tablets. For effective protection and prevention, a dosage unit of this formulation will preferably be from 0.5 g to 10 g. The doses and these individual ingredients can be varied by up to 50% of the above values, preferably varying by no more than 25%. For therapeutic propose and treatment, a dosage or multi-dosages of 1 g to 20 g per day is sufficient and effective for patients.

In yet another preferred form, a sterile injectable solutions can be prepared by incorporating crocin and crocetin prepared under pharmaceutical procedure in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of crocin and crocetin plus any additional desired ingredient from a previously sterile-filtered solution thereof. One example formulation includes preparation of a solution with crocin and/or crocetin, which is purified under pharmaceutical grade conditions, and cyclodextrin, or mannitol, or sorbitol or maltitol, fill in glass vials with designated volume/dosage and freeze-dry to get powder form and aseptically seal the vials. An injectable solution is re-constituted with sterile injectable water or saline or 5% dextrin before injection. Dosage of purified crocin and/or crocetin ranges from 10 mg to 5000 mg per day, preferably 50 mg to 1000 mg per day, more preferably 100 mg to 500 mg per days.

A topical formulation of this invention, one exampled composition contains a combination of crocin, crocetin, and one or more α-lipoic acid, a carnosine, and a carnitine, is particularly advantageous because of the multi-pronged effect these ingredients have for addressing the aging process. Each of α-lipoic acid, L-carnitine, and carnosine are produced by the body and their secretion generally decrease with age, and the topical application of these or related compounds provides protection against loss due to age. These ingredients are also antioxidants.

The topical formulation will preferably comprise crocin and/or crocetin thereof in an amount of from about 0.01 to 50% by weight, based on the total weight of the composition, or more preferably in an amount of from about 0.1 to 7.0% by weight, based on the total weight of the composition. The formulation will preferably comprise L-carnitine thereof in an amount of from about 0.01 to 50% by weight, based on the total weight of the composition, or more preferably in an amount of from about 0.5 to 2.0% by weight, based on the total weight of the composition. The formulation will preferably comprise carnosine thereof in an amount of from about 0.01 to 50% by weight, based on the total weight of the composition, or more preferably in an amount of from about 0.1 to 5.0% by weight, based on the total weight of the composition.

Following examples are presented to further explain and illustrate the invention and are not to be taken as limiting in any regard. Unless otherwise indicated, all parts and percentages are by weight.

COMPOSITION EXAMPLES

Example 1

This example provides a preferred, but not limited, dosage form of a composition of the invention. Gelatin or vegan capsules are produced by preparing a mixture of the following ingredients with filler by grinding under a vacuum to assure intimate mixing and a dry character, and then filling individual gelatin capsules with a total of 1000 mg as comprising of following:

| | |
|---|---|
| 200 mg | crocin and/or crocetin |
| 150 mg | green tea extract |
| 50 mg | curcumin |
| 50 mg | resveratrol |
| 25 mg | Panax ginseng extract |
| 15 mg | α-lipoic acid, and |
| 10 mg | L-carnitine |

These capsules are consumed in a regimen effective to prevent or treat cancers and other conditions and diseases, preferably taking once in the morning and once in the evening.

Example 2

This example provides another preferred, but not limited, composition of this invention. Tablets are produced by preparing a mixture of the following ingredients with excipient through steps by blending, dry granulating, milling, blending, compressing, and coating. A composition comprises enriched and purified crocin and/or crocetin and other phytochemicals or extracts as following:

| | |
|---|---|
| 200 mg | crocin and/or crocetin |
| 200 mg | green tea extract |
| 100 mg | curcumin |
| 100 mg | Grape seed extract |
| 50 mg | Panax ginseng extract |
| 50 mg | Rhodiola rosea extract |
| 50 mg | Ginkgo biloba extract |

A daily supplement dosage of 100 mg to 1000 mg is useful in preventing and delaying cancers and neurodegenerative diseases, enhancing brain and mental health, improving cognitive, learning and memory ability, protecting liver, heart, lung, kidney, eye, skin, nerves, normal cells.

Example 3

This example provides a preferred, but not limited, dosage form of a composition of the invention. Gelatin or vegan capsules are produced by preparing a mixture of the following ingredients with filler by grinding under a vacuum to assure intimate mixing and a dry character, and then filling individual gelatin capsules with a total of 1000 mg as comprising of following:

| | |
|---|---|
| 200 mg | crocin and/or crocetin |
| 500 mg | dihydromyricetin |
| 50 mg | resveratrol |
| 50 mg | artichoke leaf extract |

These capsules are consumed in a regimen effective to protect liver from injury and alcohol damage, or treat liver cancer and/or restore liver function, prevent and/or treat other conditions and diseases, preferably taking once in the morning and once in the evening, or preferably taking prior to consume alcohol.

Example 4

This example provides a preferred, but not limited, dosage form of a composition of the invention. Gelatin or vegan capsules are produced by preparing a mixture of the following ingredients with filler by grinding under a vacuum to assure intimate mixing and a dry character, and then filling individual gelatin capsules with a total of 1000 mg as comprising of following:

| | |
|---|---|
| 250 mg | crocin and/or crocetin |
| 200 mg | citrus extract (90% polymethoxylated flavones, nobiletin & tangeretin) |
| 100 mg | curcumin |
| 50 mg | resveratrol |

These capsules are consumed in a regimen effective for prevention and treatment of cancer and lowering risk of cancers and other diseases or conditions, preferably taking once in the morning and once in the evening in the middle of meal.

Example 5

This example provides a preferred, but not limited, composition of this invention for eye health. Tablets are prepared by preparing a mixture of the following ingredients with excipient through steps by blending, dry granulating, milling, blending, compressing, and coating. A composition comprises enriched and purified crocin and/or crocetin and other phytochemicals or extracts as following:

| | |
|---|---|
| 200 mg | crocin and/or crocetin |
| 200 mg | lycopene |
| 100 mg | beta-carotene |
| 100 mg | bilberry extract |
| 50 mg | lutein |
| 25 mg | zeaxanthin |

These tablets are consumed in a regimen effective to prevent and treat of age-related macular degeneration (AMD), increase blood circulation in retina, protect retina and brain from toxin- or light-induced stress, improve and maintain eye sight and brain function, and lower risk of cancers and other diseases or conditions, preferably taking once in the morning and once in the evening in the middle of meal.

Example 6

This example provides a preferred, but not limited, therapeutically injectable/infusion composition of this invention. A sterile injectable/infusion composition is prepared in amber vials or bottles in lyophilized powder form by steps: quantitatively mixing 5 g high purity crocin and/or crocetin (at least a purity of 98%, preferably at least 99%) with 20 g or 40 g pharmaceutical grade mannitol, dissolving the mixture in a suitable solvent 400 ml or 800 ml distilled or injectable water, sterilizing by filtering the solution through 0.15-0.22 μm sterilized filtration membrane, distributing into sterilized amber vials or bottles, freeze-drying, sealing vials or bottles, and labeling and packing to obtain the products. To inject or infuse the product to a subject, a solution of the product is reconstituted by adding, shaking and dissolving in suitable amount of injectable water or physiological (0.7% w/w) saline solution.

A. A Reconstituted Injection Lyophilized Vial Contains:

| | |
|---|---|
| 50 mg | crocin and/or crocetin |
| 200 mg | mannitol |
| 5 ml | physiological (0.7% w/w) saline solution |

B. A Reconstituted Infusion Lyophilized Bottle Contains:

| | |
|---|---|
| 250 mg | crocin and/or crocetin |
| 2000 mg | mannitol |
| 50 ml | physiological (0.7% w/w) saline solution |

This injectable or infusion form of this invention is useful in treating various cancers, neurodegenerative disorders such as Alzheimer's and Parkinson's diseases, other diseases and conditions.

Example 7

This example provides a preferred, but not limited, dosage form of a composition of this invention. Effervescent tablets are prepared by following steps: a. mix anhydrous citric acid with crocin and/or crocetin. b. make granulates by adding 65% citric acid solution under agitation and subsequently drying at low temperature to relative humidity of the granule to less than 0.15%. c. mix granules at low humidity with anhydrous sodium bicarbonate, flavorant, aspartame, and polyethylene glycol (PEG) 6000. d. press to form the effervescent tablets and magnesium stearate is used as an external lubricant to avoid sticking during the tableting operation. Average size of the tablets is 3.85 g with diameter of 23 mm and thickness of 3.15 to 3.25 mm. e. pack 10 tablets in a re-sealable HDPE container. An exemplary effervescent composition comprises the following:

| | |
|---|---|
| 200 mg | crocin and/or crocetin |
| 250 mg | dihydromyricetin |
| 5700 mg | anhydrous citric acid |
| 12000 mg | sodium bicarbonate |
| 300 mg | PEG 6000 |
| 200 mg | flavorant (lemon flavor) |
| 200 mg | aspartame |

A daily consumption of one tablet by dissolving the tablet in 6 oz. of water at room temperature and drinking is useful and effective for protecting liver from alcohol or over dose iron or other heavy metal caused damages, protecting lung from injury or cancers caused by smoke or smog, enhancing heart functions, preventing or treating cancers or other diseases or conditions.

Example 8

This example provides a preferred, but not limited, dosage form of a composition of this invention for application in food or drink. Powder of crocin and/or crocetin with rebaudioside A, glycyrrhizic acid ammonium salt, and erythritol in a ratio of 25:50:50:2875 by weight is mixed. The pre-mixed powder product can be directly used as powder form packed in sachets or packets or a moisture and light shield container with a size pre-determined scoop. The pre-mixed powder can also be further formulated and processed as cubes, granules for use in sachets or packets, and tablets. 2.5 grams of the pre-mixed powder is added to a serving of non-fat and non-sugar yogurt (6 oz.) and followed with stirring to homogenous. A nice yellow colored and sweetened yogurt with 25 mg crocin and/or crocetin but no extra calories is served. In application to a drink, 2.5 grams of the pre-mixed powder or formed cubes, granules or tablets, which are readily soluble, is added to a serving (8 oz.) of water, or drink or juice. Flavoring can be added at user's choice or preference. Stir with a spoon for 1 to 5 minutes. A drink with 25 mg crocin and/or crocetin but no extra calories is served. A composition list is provided as comprising of following:

| | |
|---|---|
| 100 mg | crocin and/or crocetin |
| 200 mg | rebaudioside A |
| 200 mg | glycyrrhizic acid ammonium salt |
| 9500 mg | erythritol |

This composition in products is consumed daily in a regimen effective for eye health and brain health, to prevent or delay age-related macular degeneration, to prevent or treat mild-to-moderate Alzheimer's disease, to prevent and reduce risks of cancers and heart diseases, and to enhance overall health.

The above description is intended to enable the person skilled in the art to practice the invention. It is not intended to detail all of the possible modifications and variations which will become apparent to the skilled worker upon reading the description. It is intended, however, that all such modifications and variations be included within the scope of the invention which is seen in the above description and otherwise defined by the following claims. The claims are meant to cover the indicated elements and steps in any arrangement or sequence which is effective to meet the objectives intended for the invention, unless the context specifically indicates the contrary.

PATENT CITATIONS

| Cited Patent | Filing date | Publication date | Applicant | Title |
|---|---|---|---|---|
| CN102516325 A | Nov. 15, 2011 | Jun. 27, 2012 | | Method for producing crocin with higher than 95% purity from gardenia |
| WO2004078695 A1 | Mar. 3, 2004 | Sep. 16, 2004 | Koichi Harada, Riken Vitamin Co, Masahiro Takahashi | Method for the purification of crocetin |
| WO2010094745 A1 | Feb. 18, 2010 | Aug. 26, 2010 | Omnica Gmbh | Hydrolysate of crocin |
| US20100210572 A1 | Feb. 17, 2010 | Aug. 19, 2010 | Thomas Eidenberger | Hydrolysate of crocin |
| WO2004056201 A1 | Dec. 19, 2002 | Jul. 8, 2004 | Shri Gopal Agarwal, Vijai Kant Agnihotri, Council Scient Ind Res, Ghulam Nabi Qazi, Om Prakash Suri, Rajinder Kumar Thappa | Method for the preparation of saffron pigment and flavor concentrate |
| U.S. Pat. No. 7,351,844 B2 | Feb. 25, 2003 | Apr. 1, 2008 | Diffusion Pharmaceuticals Llc | Bipolar trans carotenoid salts and their uses |
| US20130156746 A1 | Aug. 25, 2011 | Jun. 20, 2013 | Persavita Ltd. | Composition and method of manufacture |
| US20110236481 A1 | Jun. 9, 2011 | Sep. 29, 2011 | Cedric Bourges | Use of saffron and/or safranal and/or crocin and/or picrocrocin and/or derivatives thereof as a satiety agent for treatment of obesity |

REFERENCE

International Agency for Research on Cancer: "Global Cancer Facts & FIGS. 2nd Edition"

American Cancer Society: "Cancer Facts & FIGS. 2012"

Chermahini S H, Majid F A A, Sarmidi M R, Taghizadeh E, Salehnezhad S. Impact of saffron as an anti-cancer and anti-tumor herb. African Journal of Pharmacy and Pharmacology 2010, 4(11): 834-840.

Bhargavak V. Medicinal uses and pharmacological properties of *Crocus sativus* Lnn (Saffron). Int. J. Pharm Pharm Sci. 2011, 3, suppl 3:22-26.

Carmona M, Zalacain A, Sanchez A M, Lovella J L, Alonso G L. Crocetin Esters, Picrocrocin and Its Related Compounds Present in *Crocus sativus* Stigmas and *Gardenia jasminoides* Fruits. Tentative Identification of Seven New Compounds by LC-ESI-MS. J. Agric. Food Chem. 2006, 54:973-979.

Chen Y, Zhang H, Tian X, Zhao C, Cai L, Liu Y, Jia L, Yin H X, Chen C. Antioxidant potential of crocins and ethanol extracts of *Gardenia jasminoides* ELLIS and *Crocus sativus* L.: A relationship investigation between antioxidant activity and crocin contents. Food Chemistry 2008, 109:484-492

Nair S C, Panikkar B and Panikkar K R: Antitumor activity of saffron (*Crocus sativus*). Cancer Lett 1991, 57: 109-114.

Nair S C, Varghese C D, Pannikar K R, Kurumboor S K, Parathod R K. Effects of saffron on vitamin A levels and its antitumor activity on the growth of solid tumors in mice. Int J Pharmacog 1994, 32(2):105-114.

Abdullaev F I, Frenkel G D. Effect of saffron on cell colony formation and cellular nucleic acid and protein synthesis. BioFactors 1992a, 3(3):201-204.

Abdullaev F I, Frenkel G D. The effect of saffron on intracellular DNA, RNA and protein synthesis in malignant and non-malignant human cells. BioFactors 1992b, 4(1):43-45.

Abdullaev F I: Cancer chemopreventive and tumoricidal properties of saffron (*Crocus sativus* L.). Exp Biol Med (Maywood) 227(1): 20-25, 2002.

Abdullaeva F I, Rivero'n-Negretea L, Caballero-Ortegaa H, Manuel Herna'ndeza J, Pe'rez-Lo'peza I, Pereda-Mirandab R, Espinosa-Aguirre J J. Use of in vitro assays to assess the potential antigenotoxic and cytotoxic effects of saffron (*Crocus sativus* L.). Toxicology in Vitro. 2003, 17: 1-6.

Chryssanthi D G, Lamari F N, Iatrou G, Pylara A, Karamanos N K, Cordopatis P. Inhibition of breast cancer cell proliferation by style constituents of different *Crocus* species. Anticancer Res. 2007, 27 (1A):357-62.

Bakshi H, Sam S, Rozati R, Sultan P, Islam T, Rathore B, Lone Z, Sharma M, Triphati J, Saxena R C. DNA fragmentation and cell cycle arrest: a hallmark of apoptosis induced by crocin from kashmiri saffron in a human pancreatic cancer cell line. Asian Pac J Cancer Prev. 2010, 11(3):675-9.

Premkumar K, Thirunavukkarasu C, Abraham S K, Santhiya S T, Ramesh A. Protective effect of saffron (*Crocus sativus* L.) aqueous extract against genetic damage induced by anti-tumor agents in mice. Hum Exp Toxicol 2006, 25(2): 79-84.

Akhondzadeh S, Sabet M S, Harirchian M H, Togha M, Cheraghmakani H, Razeghi S, Hejazi S S, Yousefi M H, Alimardani R, Jamshidi A. A 22-week, multicenter, randomized, double-blind controlled trial of *Crocus sativus* in the treatment of mild-to-moderate Alzheimer's disease. Psychopharmacology 2010, 207(4): 637-643.

Zhang Y, Shoyama Y, Sugiura M, Saito H. Effects of *Crocus sativus* L. on the ethanol-induced impairment of passive avoidance performances in mice. Biol Pharm Bull. 1994, 17 (2):217-21.

Abe K, Saito H. Effects of saffron extract and its constituent crocin on learning behaviour and long-term potentiation. Phytother Res. 2000, 14(3):149-52.

Maccarone R, Di Marco S, Bisti S. Saffron supplement maintains morphology and function after exposure to damaging light in mammalian retina. Invest Ophthalmol Vis Sci. 2008, 49(3):1254-61.

Falsini B, Piccardi M, Minnella A, Savastano C, Capoluongo E, Fadda A, Balestrazzi E, Maccarone R, Bisti S. Saffron supplementation improves retinal flicker sensitivity in early age-related macular degeneration. Invest Ophthalmol Vis Sci. 2010, 51: 6118-6124.

Piccardi M, Marangoni D, Minnella A M, Savastano M C, Valentini P, Ambrosio L, Capoluongo E, Maccarone R, Bisti S, Falsini B. A longitudinal follow-up study of saffron supplementation in early age-related macular degeneration: sustained benefits to central retinal function. Evid Based Complement Alternat Med. 2012, 2012: 429124.

Alonso G L, Salinas M R, Garijo J, Sanchez-Fernandez M A. Composition of crocins and picocrocin from Spanish saffron. J. Food Quality. 2001, 24:219-233.

Lechtenberg M, Schepmann D, Niehues M, Hellenbrand N, Wünsch B, Hensel A. Quality and Functionality of Saffron: Quality Control, Species Assortment and Affinity of Extract and Isolated Saffron Compounds to NMDA and σ1 (Sigma-1) Receptors. Planta Med 2008; 74: 764-772.

Baur J A, Sinclair D A. Therapeutic potential of resveratrol: the in vivo evidence. Nature Reviews Drug Discovery. 2006, 5: 493-506.

Aggarwal B B, Surh Y J, Shoshodia S. The Molecular Targets and Therapeutic Uses of Curcumin in Health and Disease. Advances in Experimental Medicine and Biology. 2007, Volume 595. Published by Springer U S.

Mukhtar H and Ahmad N. Tea polyphenols: prevention of cancer and optimizing health 1, 2, 3. Am J Clin Nutr June 2000, 71(6): 1698-1702.

He J, Giusti M M. Anthocyanins: Natural Colorants with Health-Promoting Properties. Food Science and Technology. 2010, 1: 163-187.

Kalt W, Hanneken A, Milbury P, Tremblay F. Recent Research on Polyphenolics in Vision and Eye Health. J. Agric. Food Chem., 2010, 58 (7): 4001-4007.

Cassidy A, O'Reilly E J, Kay C, Sampson L, Franz M, Forman J P, Curhan G, Rimm E B. Habitual intake of flavonoid subclasses and incident hypertension in adults. Am. J. Cli. Nutri. 2011, 93: 338-347.

Gao X, Cassidy A, Schwarzschild M A, MD, Rimm E B, Ascherio A. Habitual intake of dietary flavonoids and risk of Parkinson disease. Neurology 2012 78(15); 1138-1145.

Gouta B, Bourges C, Paineau-Dubreuil S. Satiereal, a *Crocus sativus* L extract, reduces snacking and increases satiety in a randomized placebo-controlled study of mildly overweight, healthy women. Nutrition Research. 2010, 30: 305-313.

The invention claimed is:

1. A nutraceutical composition for inhibiting, mitigating, or treating a liver disease or condition, comprising: 1-50% by weight of crocin or crocetin or both, wherein crocin and/or crocetin is extracted, enriched and/or purified from *gardenia* fruit or *gardenia* yellow by the following steps: (a) dissolving *gardenia* fruit extract or *gardenia* yellow in 50-95% ethanol at temperature range from 10° C. to 60° C.: (b) filtration, crystallization and re-crystallization at temperature range from −10° C. to 4° C., optionally followed by further purification, to provide the crocin, crocetin or both with a purity of at least 50% up to 99%; 10-75% dihydromyricetin; 0.5-20% by weight of resveratrol; 0.5-20% by weight of black tea extract; and 0.5-20% by weight of artichoke leaf extract, wherein the composition is in the form of a tablet, soft gel, capsule, pill, caplet, dragee, effervescent tablet, emulsion, gum, chewing gum, gummy candy, taffy, caramel candy, fudge, degradable thin film, nondegradable thin film, or hard candy.

2. The nutraceutical composition according to claim 1, wherein the composition comprises 0.5-30% by weight of crocin, crocetin or both, 10-60% by weight of citric acid, 5-40% by weight of potassium bicarbonate, 5-40% by weight of sodium bicarbonate, 0.5-20% by weight of sodium carbonate, 0.2-10% by weight of polyethylene glycol, 0.1-8% by weight of aspartame, and 0.1-5% by weight of a flavorant, wherein the composition is in the form of an effervescent tablet.

3. The nutraceutical composition according to claim 1, further comprises at least one ingredient selected from the group consisting of curcumin, lutein, zeaxanthin, lycopene, β-carotene, pterostilbene, nobiletin, tangeretin, α-lipoic acid, L-carnitine, carnosine, astragaloside, cycloastragenol, theaflavin, green tea extract, theaflavin-3,3'-digallate, theaflavin-3-gallate, theaflavin-3'-gallate, anthocyanidins, anthocyanins, grape extract, grape seed extract, bilberry extract, blue berry extract, rhodiola extract, *ginseng* extract, *Ginkgo biloba* extract, epimedium extract, lemon extract, licorice extract, citrus fruit extract, and *stevia* extract.

\* \* \* \* \*